(12) United States Patent
Sattmann

(10) Patent No.: US 7,748,258 B2
(45) Date of Patent: Jul. 6, 2010

(54) IMMERSION LANCE FOR ANALYSIS OF MELTS AND LIQUIDS

(75) Inventor: Ralph Sattmann, Aschaffenburg (DE)

(73) Assignee: Heraeus Electro-Nite International N.V., Houthalen (BE)

( * ) Notice: Subject to any disclaimer, the term of this patent is extended or adjusted under 35 U.S.C. 154(b) by 261 days.

(21) Appl. No.: 11/863,966

(22) Filed: Sep. 28, 2007

(65) Prior Publication Data

US 2008/0083269 A1    Apr. 10, 2008

(30) Foreign Application Priority Data

Oct. 6, 2006    (DE) ........................ 10 2006 047 765

(51) Int. Cl.
*G01N 1/00* (2006.01)
*G01K 1/12* (2006.01)

(52) U.S. Cl. ..................................... 73/64.56; 374/140

(58) Field of Classification Search ................ 73/64.56; 356/436; 374/140
See application file for complete search history.

(56) References Cited

U.S. PATENT DOCUMENTS

| 3,780,583 | A | * | 12/1973 | Poferl et al. ................. 374/140 |
| 4,046,016 | A | * | 9/1977 | Hackett .................... 73/864.57 |
| 4,152,075 | A | | 5/1979 | Rellstab |
| 4,692,556 | A | * | 9/1987 | Bollen et al. ................ 136/234 |
| 5,577,841 | A | * | 11/1996 | Wall ........................... 374/140 |
| 5,694,206 | A | | 12/1997 | Curtiss |
| 5,712,710 | A | | 1/1998 | Karakus et al. |
| 6,142,664 | A | * | 11/2000 | Ikawa et al. ................ 374/140 |
| 6,514,394 | B1 | * | 2/2003 | Vangrunderbeek et al. .. 204/400 |
| 7,365,841 | B2 | * | 4/2008 | Plessers et al. .............. 356/311 |
| 7,370,544 | B2 | * | 5/2008 | Neyens et al. ............. 73/864.59 |
| 7,384,192 | B2 | * | 6/2008 | Dams et al. ................. 374/139 |

FOREIGN PATENT DOCUMENTS

DE    103 59 447 A1    7/2005
WO   03/081287 A2    10/2003

* cited by examiner

*Primary Examiner*—John Fitzgerald
(74) *Attorney, Agent, or Firm*—Panitch Schwarze Belisario & Nadel LLP

(57) ABSTRACT

An immersion sensor for analysis of liquids or melts includes an immersion carrier, a detector and a radiation-guiding unit, and a sample chamber arranged in the immersion carrier. The sample chamber has an inlet opening for liquid or melt, and the sensing components for measurement of the liquid or melt act inside the sample chamber.

14 Claims, 6 Drawing Sheets

IMMERSION LANCE FOR ANALYSIS OF MELTS AND LIQUIDS

BACKGROUND OF THE INVENTION

The invention relates to an immersion sensor for analysis of liquids or melts with an immersion carrier comprising a sample chamber having an inlet opening arranged in the immersion carrier.

Immersion sensors are already known in various configurations. Thus, International Application Publication No. WO 03/081287 A2 describes a carrier tube, which is immersed in an aluminum melt. A lens system is arranged inside the carrier tube. At the upper end of the tube there is an optical fiber, which is connected to a spectrograph on one side and to a laser on the other side via an optical system. The radiation emitted by the melt is guided via the optical fiber into the spectrograph; there the radiation is analyzed, in order to derive therefrom analysis results on the composition of the aluminum melt.

German published patent application DE 103 59 447 A1 likewise describes an immersion sensor for analysis of molten metals with an immersion carrier, a detector, a radiation-guiding device for receiving and transmitting radiation, and a signal interface arranged on or in the immersion carrier. Here, the signal interface is connected to the detector.

BRIEF SUMMARY OF THE INVENTION

An object of the present invention is to improve existing devices, to simplify handling, and to allow a more precise analysis of melts and/or liquids.

This object is achieved by the immersion sensor according to the invention for analysis of liquids or melts with an immersion carrier, the immersion sensor having a sample chamber with an inlet opening arranged in the immersion carrier, and the sensing component or components for measuring the liquid or melt act in the sample chamber; that is, the analysis takes place in the sample chamber.

The liquids or melts preferably include glass or metal melts, particularly aluminum or steel melts. In the following, reference will often be made simply to a melt, but it will be understood that the disclosure applies to other liquids also, unless the context indicates otherwise.

The sensor is directed toward a pre-determined point in the sample chamber. The analysis takes place at this point. The liquid or melt to be analyzed is fed to this point, so that the free surface lies in the measurement area of the sensor.

For the analysis, an excitation of the liquid or melt can occur. Here, for example, a beam is generated by a beam-generating unit and directed toward the pre-determined point in the sample chamber. For the beam a laser beam can be used, but instead other beam types are definitely conceivable. The beam generates particles and/or radiation at the defined measurement point, which are emitted and guided to a collection device. For the collection device, in particular, a detector, a radiation converter, a spectrometer, an X-ray spectrometer or a mass spectrometer can be used. The measurement can be performed optically, for example as a temperature measurement, or for determining the chemical composition, for example by LIBS (laser-induced breakdown spectroscopy).

An analysis in a sample chamber leads to particularly precise measurement results, since in the region of the measurement point a gas atmosphere suitable for the analysis can be produced without thereby changing the position of the measurement point.

With an analysis inside the sample chamber, waves and movements of the melt, which falsify the measurement results, are also avoided. The analysis on the flowing liquid or melt reduces any influences by the measurement itself, e.g., an enrichment or depletion of individual elements by the excitation, and produces a greater accuracy of the analysis than when the same sample volume is always used, or when the composition of the melt or liquid is changed by the measurement itself.

Here, analysis will be understood to be measurement, that is, determination of a value through quantitative comparison of the measurement parameter with a scale, particularly of chemical or physical values.

An immersion sensor according to the invention allows analyses and measurements of the melt at different points in the melt, since a change of position of the sensor can be easily carried out.

Advantageously, the sensor is directed toward a predefined measurement point inside the sample chamber, at which the freshly inlet melt or liquid is guided past. This guarantees a defined distance between the sensor and the melt surface. This leads to particularly precise and comparable results.

An advantageous embodiment of the invention provides that the predefined measurement point lies at an inlet opening of the melt into the sample chamber. It has been shown that a precise measurement of the composition of the melt is thereby possible, because fresh melt is constantly supplied and only a very minimal cooling of the melt occurs. The accuracy is improved, and at the same time a change in the composition of the melt by the analysis is prevented, because fresh melt is always supplied.

Advantageously, the measurement point is arranged at or on an analysis plate. The analysis plate likewise allows a defined distance between the sensor and melt. The analysis plate also results in the flow rate of the melt being reduced and the surface of the melt being increased, and thus a more precise analysis can occur.

Advantageously, the inlet opening is an inlet tube. It has been shown that an inlet tube can ensure that during the predominant period of the analysis only a pure melt is supplied to the measurement point. Slag and other deposits that falsify the analysis result are prevented. The inlet tube can also be shaped such that the inlet flow rate of the melt is reduced. Thus, the inlet flow rate can be controlled, for example by a bending or narrowing of the inlet tube.

The melt is collected in the sample chamber beneath the measurement point.

Advantageously, the immersion sensor has a melt level detector. This melt level detector measures the level of the melt in the sample chamber and allows the sensor to be pulled from the melt when the sample chamber is filled with melt up to a defined level. Damage to the sensor and the optics contained in the sensor can thereby be prevented. Such melt level detectors can include contact probes, ultrasound sensors, optical sensors, or the like. Here, all other devices are conceivable, which allow a measurement of the level.

It is definitely conceivable that the level detector may be connected to a device, which allows an automatic removal of the sensor from the melt at a defined level.

Here, it is further advantageous if the optics or other sensitive parts are protected against spray or vapors of the melt by a protective window.

It is advantageous if the immersion carrier is constructed as a tube. The individual parts can thereby be easily arranged in the immersion sensor and are protected during transport.

Advantageously, the detector has a device for receiving radiation and for converting it into electrical signals. In particular, the detector is designed for receiving and converting visible light, ultraviolet radiation, infrared radiation, X-ray radiation, and/or microwave radiation into electrical signals. Consequently, all types of optical or other radiation can be received and used for analyzing the melt.

It is advantageous if an optical spectrometer, an X-ray spectrometer, and/or a mass spectrometer is arranged on or in the immersion carrier.

An advantageous construction of the invention provides that the immersion sensor have a modular design, preferably in two parts. In this way, one part, advantageously the upper part, is a reusable part, which contains the devices for analysis. The lower part is designed for one-time use and contains the sample chamber. The upper, reusable part can remain completely above the melt during the analysis process.

In order to protect the immersion sensor from the heat, it is advantageous if the immersion sensor is water-cooled. Longer analysis times are thereby allowed, which leads to more precise analysis results.

It is advantageous if the immersion sensor has a protective cap, which is located at the inlet opening and which melts away only after a certain period after immersion. In this way it can be ensured that only clean melts, that is no slag, reach the measurement point, and a precise measurement and analysis are allowed.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

In the drawings, the same reference numerals are used to illustrate similar or like elements, but for sake of clarity not all elements are labeled in each Figure, it being understood that unlabeled elements are the same or similar to those labeled in other Figures.

DETAILED DESCRIPTION OF THE INVENTION

Figure 1:
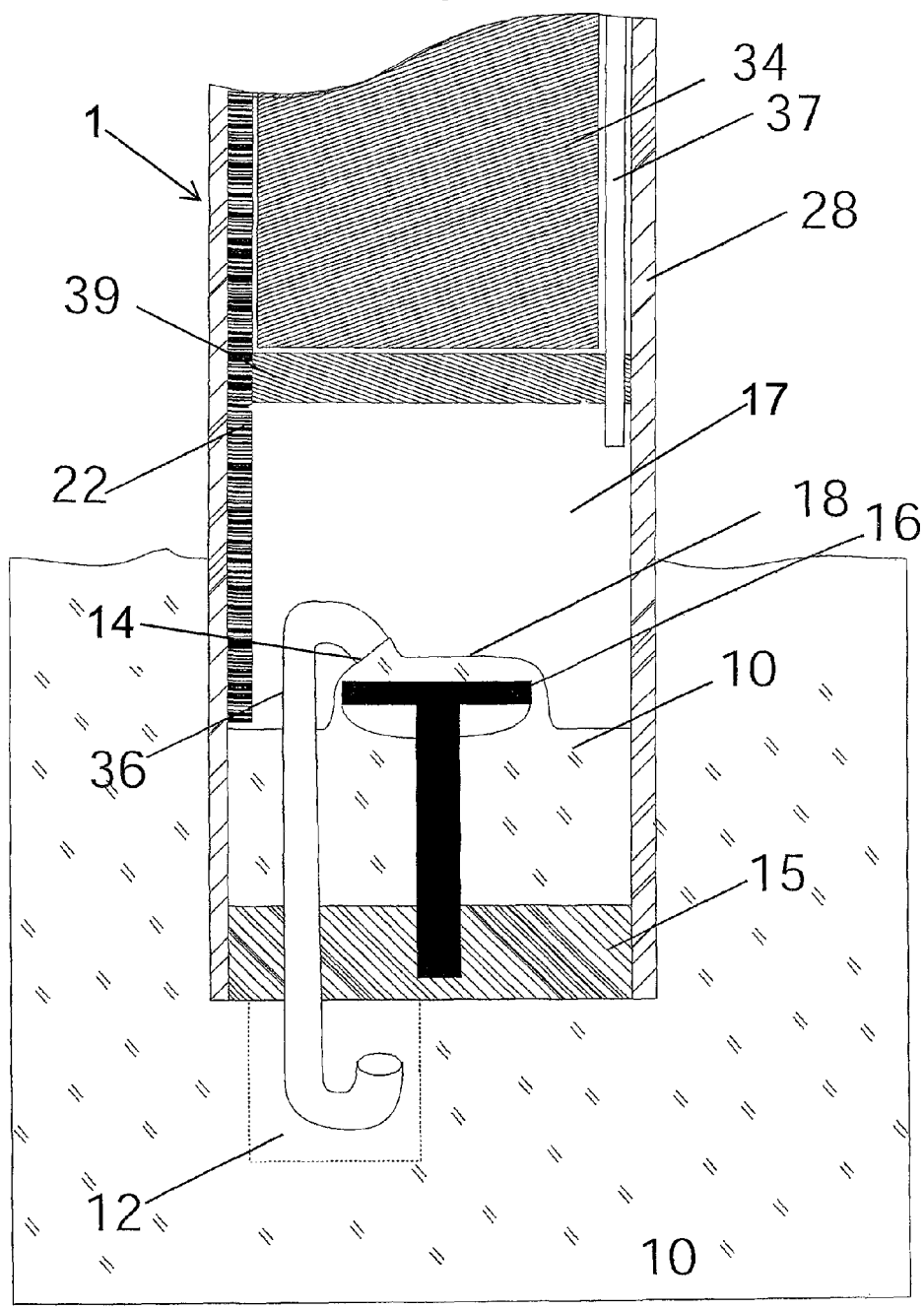
FIG. 1 is schematic, cross-sectional view through an immersion sensor according to one embodiment of the invention with its immersion end dipped in a liquid or melt.

FIG. 1 shows an immersion sensor 1 according to one embodiment of the invention in cross section. The immersion sensor 1 is surrounded by a protective tube 28. At the lower end of the immersion sensor 1 the sample chamber 17 is located. Inside the sample chamber 17 there is a melt level detector 22, a sample plate 16, and an inlet opening 14, which is formed in this case by an inlet tube 36. The end of the inlet tube 36 facing the melt 10 is provided with a protective cap 12, which melts away after the immersion sensor 1 is immersed in the melt 10 and thus ensures that only clean melt 10 reaches the measurement point 18. Upon immersion of the immersion sensor 1 into the melt 10, the protective cap 12 dissolves and the melt 10 enters the sample chamber 17 through the inlet opening 14. When the melt 10 enters the sample chamber 17, the melt 10 is analyzed at a defined measurement point 18. The measurement point 18 is arranged in FIG. 1 on a sample plate 16. Here, the sample plate 16 can be arranged at any desired position inside the sample chamber 17. The melt 10, which enters through the inlet opening 14 into the sample chamber 17, is collected on the floor 15 of the sample chamber 17. If necessary, this collected melt can also be removed when the immersion sensor 1 is removed from the melt 10 and used for additional analyses. In the upper part of the immersion sensor 1 are located the optics 34 and also a gas conduit 37 for supplying gas, in order to allow a certain pressure inside the sample chamber 17.

Figure 2:
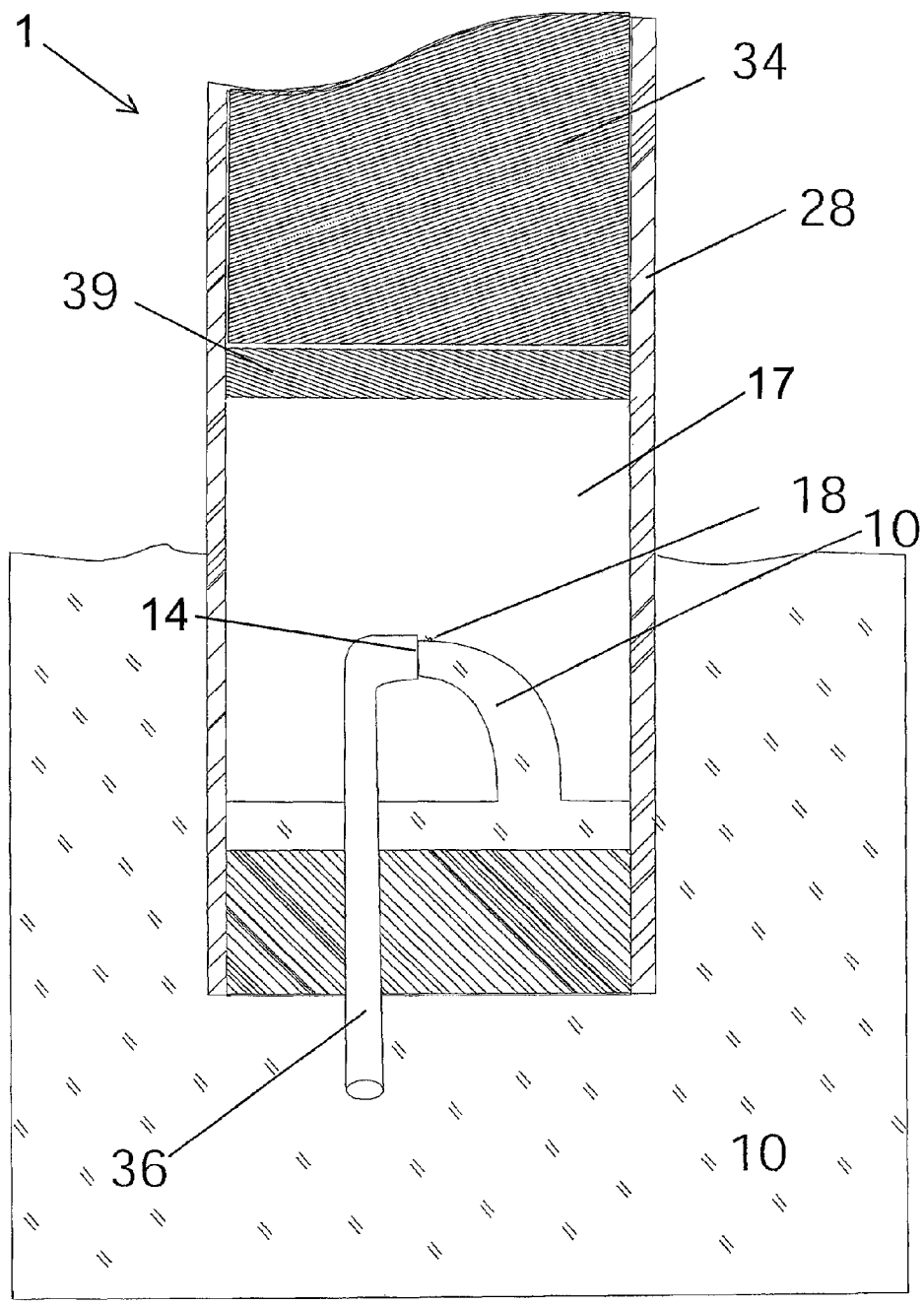
FIG. 2 is a view similar to FIG. 1 of another embodiment an immersion sensor according to the invention, illustrating the measurement point without a sample plate.

FIG. 2 shows the view of another embodiment of the sample chamber 17 with measurement point 18. Here, the measurement point 18 is not arranged on a sample plate 16, but instead the measurement of the melt 10 occurs at its entry from the inlet opening 14 into the sample chamber 17. The entry of the melt 10 occurs through an inlet tube 36.

Figure 3:
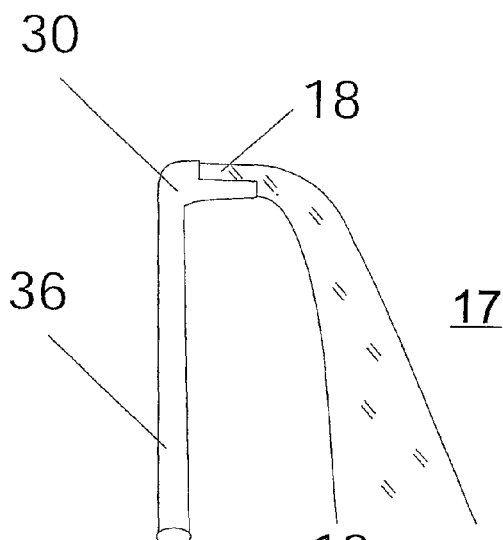
FIGS. 3a, 3b and 3c are schematic representations of various constructions of the inlet tube and sample plate for the sample chamber according to embodiments of the invention.
Figure 3:
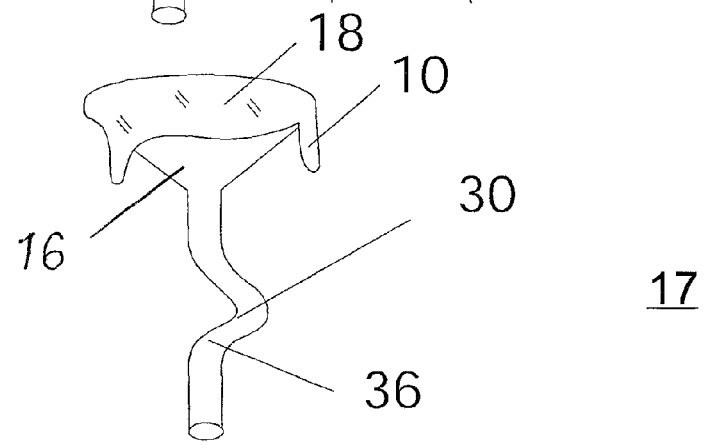
Figure 3:
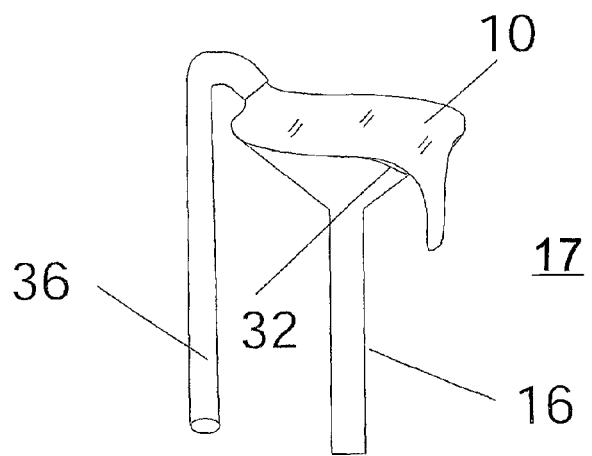

FIGS. 3a, b and c show various constructions of the inlet tube 36. In FIG. 3a the inlet tube 36 is formed such that the melt 10 must flow through an arc 30. Here, the inlet tube 36 has at its end located in the sample chamber 17 a region which is milled off at the top. In this region the melt 10 can be analyzed particularly well, because this region forms a sort of sample plate 16.

FIG. 3b shows another construction of the inlet tube 36. Here, the inlet tube 36 has an arc 30, which should prevent the melt 10 from flowing too quickly into the sample chamber 17. The upper region of the inlet tube 36 is formed as the sample plate 16. The melt 10 flows over the edge of the sample plate 16, and thus reaches the sample chamber 17. The measurement of the melt 10 can occur either on the sample plate 16 or upon overflowing of the melt 10 past the edge of the sample plate 16.

In FIG. 3c another possibility is shown for how the melt 10 can be analyzed. The melt 10 reaches the sample chamber 17 via an inlet tube 36 and there flows onto a sample plate 16. The sample plate 16 has an overflow channel 32, at which the controlled discharge of the melt 10 occurs.

If necessary, the sample plate 16 can be flat, high-crowned at the outside or high-crowned in the middle, or can have a complicated shape and special features, as for example the overflow channel 32. Here, the inlet tube 36 and sample plate 16 can be separate components or can be integrated monolithically into the sample chamber 17. In order to minimize contamination of the melt 10 before the analysis, pure quartz glass can be used as the inlet tube 36. Instead, cement, ceramics, or similar materials are also conceivable here as the inlet tube 36 and sample plate 16.

Figure 4:
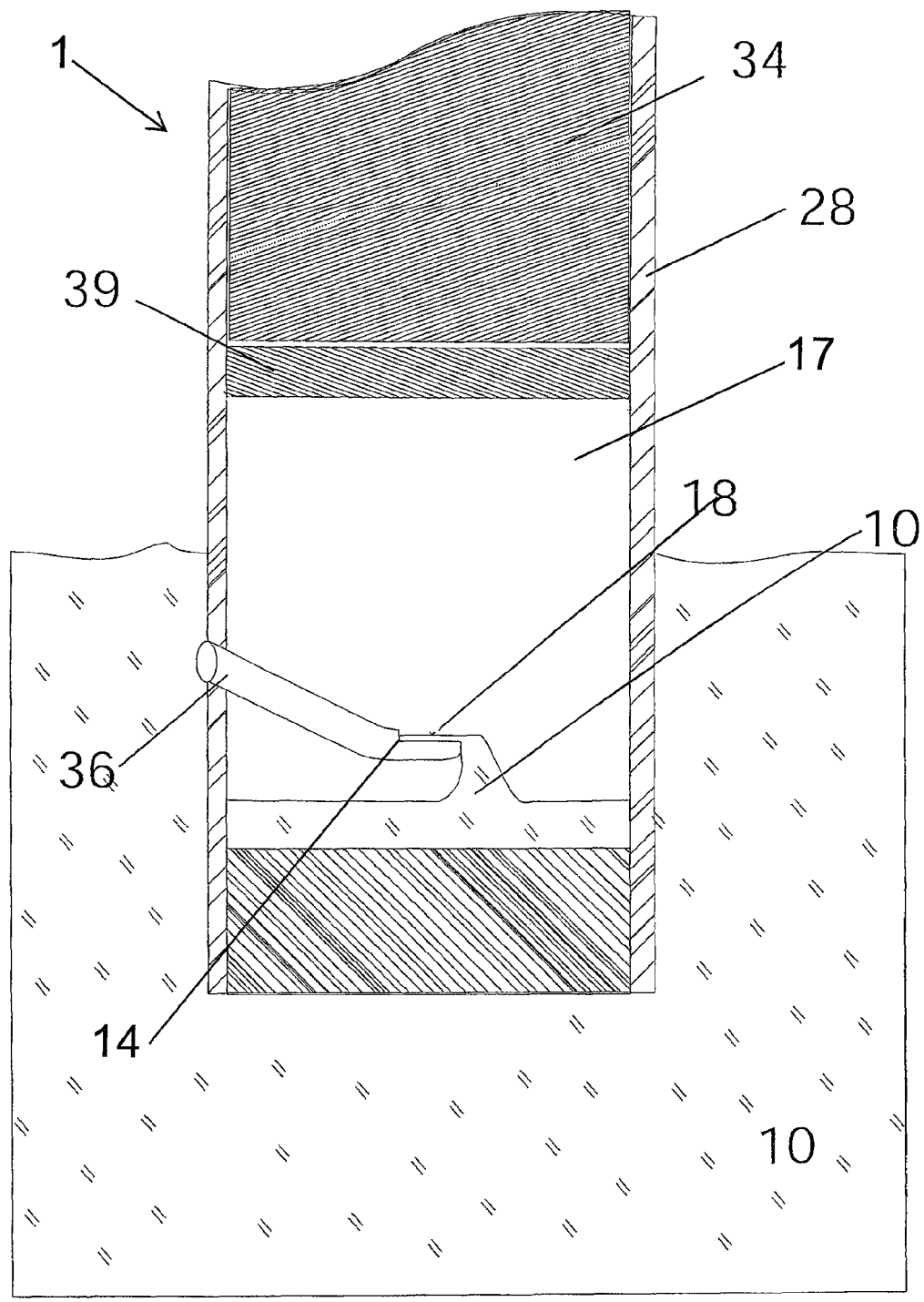
FIG. 4 is a view similar to FIG. 1 of a further embodiment of an immersion sensor according to the invention, illustrating the sample chamber with a different arrangement of the measurement point.

FIG. 4 shows another embodiment of the sample chamber 17 with measurement point 18. Here, the melt 10 is introduced into the sample chamber 17 via an inlet tube 36, which is located at the side of the immersion sensor 1. The measurement occurs here when the melt 10 comes out of the inlet tube 36. Here, it is conceivable that the melt 10 can also flow onto a sample plate.

Figure 5:
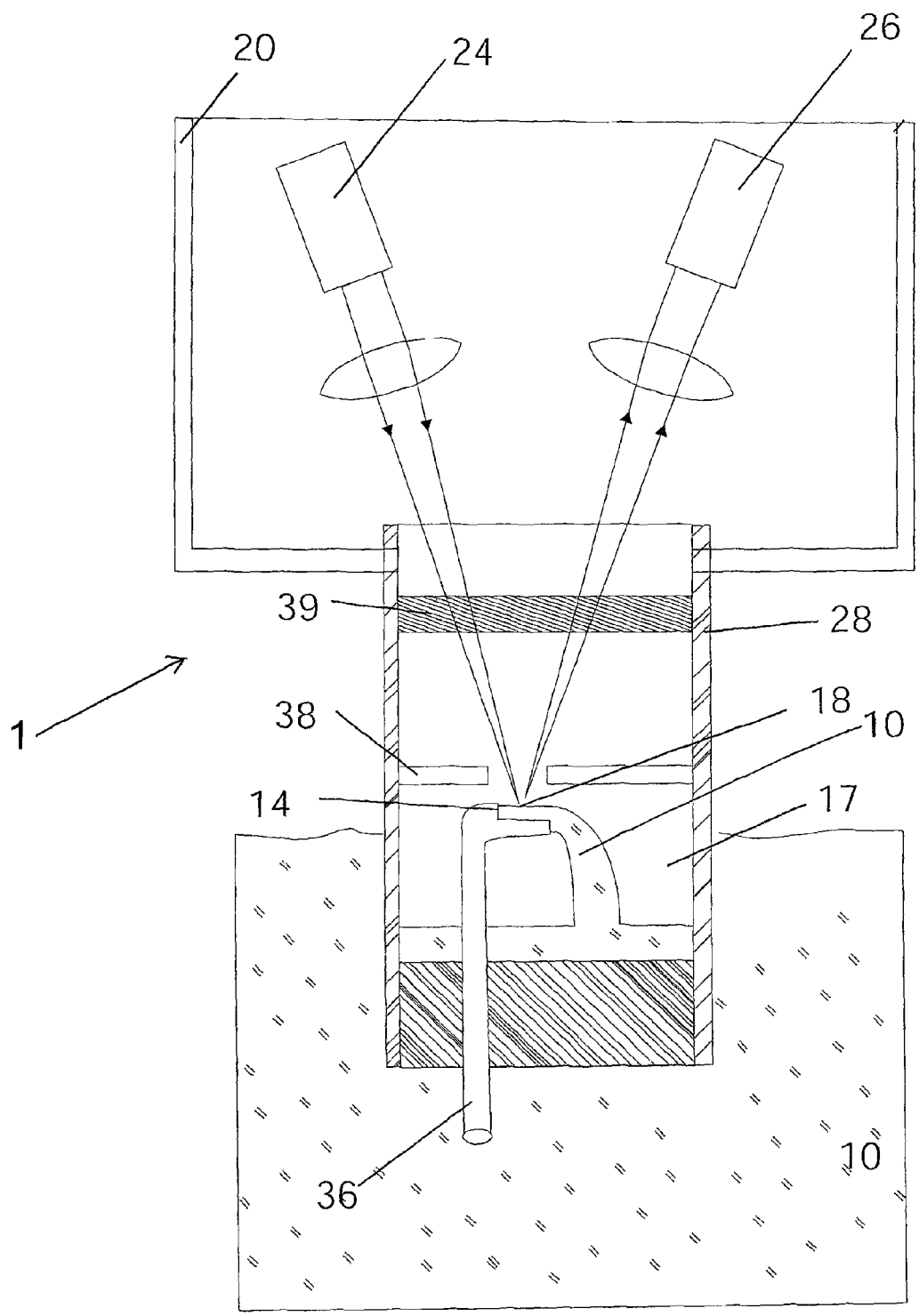
FIG. 5 is schematic cross-sectional view of a device for measurement and analysis of melts using an immersion sensor according to one embodiment of the invention.

FIG. 5 shows a device for measurement and analysis of melts. The immersion sensor 1 shown here has an upper, reusable part 20 and a lower part. Inside the immersion sensor 1 is located a laser 24 and a spectrometer 26. The immersion sensor 1 has a housing 28, which can be water-cooled. In the lower part of the immersion sensor 1 is located the inlet opening 14 with an inlet tube 36, through which the melt 10 comes into the sample chamber 17 when the immersion sensor 1 is immersed into the melt 10. Here, a quartz glass disk 38 having an opening for the laser and analysis beams and a protective window 39 are used for protecting the laser 24 from vapors or heat radiation of the melt 10.

Figure 6:
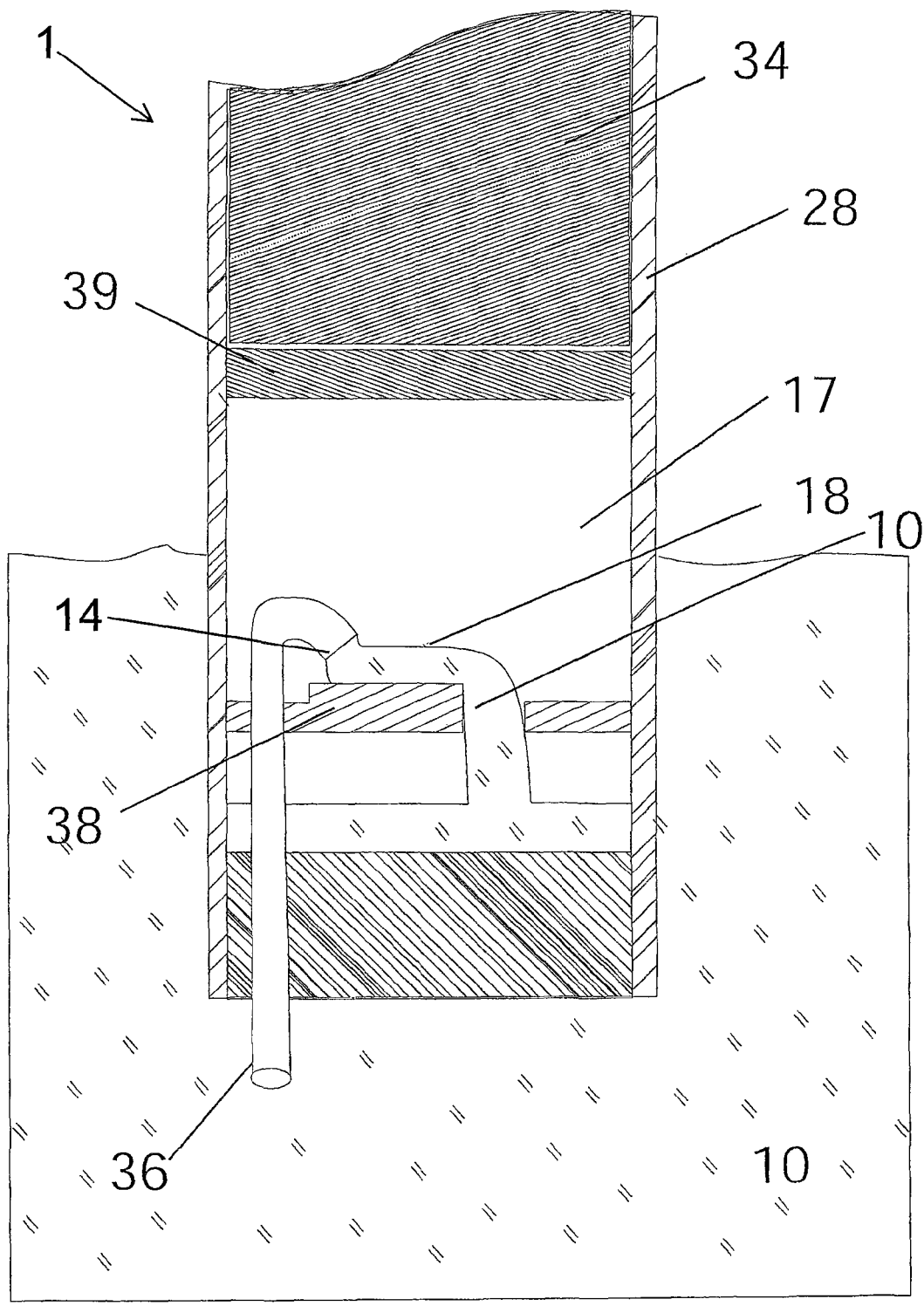
FIG. 6 is a view similar to FIG. 1 of a still further embodiment of an immersion sensor according to the invention, illustrating another arrangement of the sample chamber with the measurement point.

In FIG. 6 another embodiment of the immersion sensor 1 according to the invention is shown. The immersion sensor 1 here has in the sample chamber 17 a plate protective plate 38, which also assumes, among other things, the function of a sample plate.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An immersion sensor for analysis of liquids or melts, the immersion sensor comprising an immersion carrier, a sample chamber arranged in the immersion carrier, an inlet opening for the liquid or melt arranged in the sample chamber, and at least one sensing component for measurement of the liquid or melt, wherein the at least one sensing component acts in the sample chamber and is directed toward a predefined measurement point inside the sample chamber, the predefined measurement point lying at the inlet opening for the liquid or melt into the sample chamber.

2. The immersion sensor according to claim 1, wherein the analysis is performed on the liquid or melt entering the sample chamber.

3. The immersion sensor according to claim 1, wherein the measurement point is arranged on an analysis plate.

4. The immersion sensor according to claim 1, further comprising a melt level detector in the sample chamber.

5. The immersion sensor according to claim 1, wherein the immersion carrier has a form of a tube.

6. The immersion sensor according to claim 1, wherein the at least one sensing component is designed to measure physical and/or chemical parameters.

7. The immersion sensor according to claim 1, wherein the at least one sensing component is arranged on or in the immersion carrier and comprises at least one of an optical spectrometer, an X-ray spectrometer, and a mass spectrometer.

8. The immersion sensor according to claim 1, wherein the at least one sensing component comprises a device for excitation of the liquid or melt with radiation.

9. The immersion sensor according to claim 1, wherein the immersion sensor has a modular construction.

10. The immersion sensor according to claim 1, further comprising a housing which is water-cooled.

11. The immersion sensor according to claim 1, wherein the inlet opening comprises an inlet tube.

12. The immersion sensor according to claim 11, wherein the inlet tube has a protective cap on an end opposite the inlet opening.

13. A method for analysis of liquids or melts using the immersion sensor according to claim 1.

14. The method according to claim 13, wherein the melt comprises molten metal.

* * * * *